United States Patent
Chow et al.

(10) Patent No.: US 8,131,472 B2
(45) Date of Patent: Mar. 6, 2012

(54) METHODS FOR HIERARCHICAL ORGANIZATION OF DATA ASSOCIATED WITH MEDICAL EVENTS IN DATABASES

(75) Inventors: Tony H. Chow, Weston, CT (US); Robert R. Friedlander, Southbury, CT (US); Anwer M. Khan, Irvine, CA (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 1542 days.

(21) Appl. No.: 10/952,016

(22) Filed: Sep. 28, 2004

(65) Prior Publication Data

US 2006/0069514 A1    Mar. 30, 2006

(51) Int. Cl.
*G01N 33/48* (2006.01)
*G01N 31/00* (2006.01)
*C12Q 3/00* (2006.01)

(52) U.S. Cl. .................... 702/19; 702/22; 435/3

(58) Field of Classification Search .............. None
See application file for complete search history.

(56) References Cited

U.S. PATENT DOCUMENTS

| | | | |
|---|---|---|---|
| 4,328,978 A | 5/1982 | McLaughlin | |
| 5,692,501 A * | 12/1997 | Minturn | 600/301 |
| 6,058,391 A | 5/2000 | Gardner | |
| 6,189,004 B1 | 2/2001 | Rassen et al. | |
| 6,385,604 B1 | 5/2002 | Bakalash et al. | |
| 6,509,898 B2 | 1/2003 | Chi et al. | |
| 6,578,043 B2 | 6/2003 | Nye | |
| 6,629,106 B1 | 9/2003 | Narayanaswamy et al. | |
| 2002/0059183 A1 | 5/2002 | Chen | |
| 2002/0099691 A1 | 7/2002 | Lore et al. | |
| 2002/0099692 A1 | 7/2002 | Shah et al. | |
| 2002/0156791 A1 | 10/2002 | Nesamoney et al. | |
| 2002/0184225 A1 | 12/2002 | Ghukasyan | |
| 2003/0074222 A1 | 4/2003 | Rosow et al. | |
| 2003/0088438 A1 | 5/2003 | Maughan et al. | |
| 2003/0126148 A1 | 7/2003 | Gropper et al. | |
| 2003/0171876 A1 * | 9/2003 | Markowitz et al. | 702/20 |

(Continued)

FOREIGN PATENT DOCUMENTS

JP    2002312373    4/2001

(Continued)

OTHER PUBLICATIONS

Wang, C., "A COBRA-based Object Framework with Patient Identification Translation and Dynamic Linking." Methods of Information in Medicine, vol. 38, No. 1, pp. 55-65, Mar. 1999. (abstract only).

(Continued)

*Primary Examiner* — Russell S Negin
(74) *Attorney, Agent, or Firm* — Yudell Isidore Ng Russell PLLC

(57) ABSTRACT

Methods of organizing medical data include hierarchically relating a single type of medical or research event to medical data generated from the single type of medical or research event in a computer database environment. Organizing the data in this way enables a researcher to access medical data collected as part of a medical procedure performed on a large number of patients, but at different times. For example, the medical data may be viewed in a more hierarchical fashion, thereby enabling the researcher to further investigate potential relationships between other factors.

20 Claims, 7 Drawing Sheets

U.S. PATENT DOCUMENTS

| | | |
|---|---|---|
| 2003/0177132 A1 | 9/2003 | Thomas et al. |
| 2003/0191699 A1 | 10/2003 | Fitzgerald et al. |
| 2003/0195898 A1 | 10/2003 | Agarwal et al. |
| 2004/0006532 A1 | 1/2004 | Lawrence et al. |
| 2004/0193572 A1 | 9/2004 | Leary |
| 2005/0102210 A1 | 5/2005 | Song et al. |

FOREIGN PATENT DOCUMENTS

| | | |
|---|---|---|
| JP | 2002342484 | 2/2002 |
| WO | WO 01/08077 A1 | 2/2001 |

OTHER PUBLICATIONS

Gabrieli, Guide for Unique Healthcare Identifier Model, Journal of Clinical Computing, vol. 21, No. 5, pp. 101-139, 1993. (abstract only).

Polak et al, "Using Automated Analysis of the Resting Twelve-Lead ECG to Identify Patients at Risk of Developing Transient Myocardial Ischaemia—an Application of an Adaptive Logic Network," Physiological Measurement, vol. 18, No. 4, pp. 317-325, Nov. 1997 (abstract only).

Adam et al., "Positive Patient Identification: a Practical Solution to a Challenging Problem," Toward an Electronic Patient '97 Conference and Exposition. Proceedings, Pt. vol. 3, pp. 100-108, 1997. (abstract only).

Chatfield, "Marketing an HMO by 'Smart' ID Cards with Patient History on an Electronic Medical Record," Proceedings. Toward an Electronic Patient Record '96. Twelfth International Symposium on the Creation of Electronic Health Record System and Global Conference on Patient Cards, Pt. vol. 1, pp. 608-620, 1996. (abstract only).

Shelfer et al., "Smart Card Evolution," *Communications of the ACM*, vol. 45, No. 7, Jul. 2002, pp. 83-88.

Grimson et al., "The SI Challenge in Health Care," *Communications of the ACM*, vol. 43, No. 6, Jun. 2000, pp. 49-55.

Lowery et al., "Barriers to Implementing Simulation in Health Care," Proceedings from the 1994 Winter Simulation Conference, pp. 868-875.

Zarowski et al., "Some Algorithms for Circadian Rhythm Identification," 2001 IEEE Pacific Rim Conference on Communications, Computers and Signal Processing, Pt. Vo 12, pp. 425-428, 2001 (abstract only).

Hoshiai et al., "SION Architecture: Semantic Information-Oriented Network Architecture," Transactions of the Institute of Electronics, Information and Communication Engineers B., vol. J84-B, No. 3, pp. 411-424, Mar. 2001 (abstract only).

Goehring, "Identification of Patients in Medical Databases—Soundex Codes Versus Match Code," Medical Informatics, vol. 10, No. 1, pp. 27-34, Jan.-Mar. 1985. (abstract only).

Goodwin, Linda et al., "Data Mining for Preterm Birth Prediction" Proceedings of the 2000 ACM Symposium on Applied Computing (Mar. 19-21, 2000—Como, Italy), vol. 1, pp. 46-51.

\* cited by examiner

METHODS FOR HIERARCHICAL ORGANIZATION OF DATA ASSOCIATED WITH MEDICAL EVENTS IN DATABASES

FIELD OF THE INVENTION

The invention relates to data processing in general and, more particularly, to organization of data.

BACKGROUND OF THE INVENTION

As the field of healthcare continues to become more specialized, the provision of services by many healthcare workers to many patients may increase. In other words, healthcare delivery has been organized into specialized departments or healthcare sources such as, for example, nursing, laboratory, pharmacy, radiology and the like. Each department has responsibility for accomplishing its particular, often specialized, subset of tasks. Sometimes the departments are associated with different healthcare enterprises or offices having different geographic locations. Accordingly, the provision of healthcare services to patients by multiple healthcare workers may result in sub-optimal healthcare operations because patient information related to a single patient, stored in various different location may not be easily accessible.

This patient information, or medical data, may be stored in a database environment configured to store large volumes of data. Furthermore, the medical data stored in the database environment may be processed by, for example, searching the unstructured medical data, such as patient test results. Details with respect to conventional methods for storing and/or accessing medical data in and/or from databases is discussed in, for example, United States Patent Publication Nos. US 2003/0088438 and US 2003/0177132.

However, as the amount of available medical data expands and becomes more unstructured, it may become increasingly difficult to store and/or access unstructured medical data. For example, as genomic data has been mapped, the amount of data that can be searched has expanded rapidly thereby increasing the difficulty of storing and accessing the medical data for purposes of diagnosing various medical conditions and/or researching medical areas. Accordingly, there is a need to improve storage of, access to and modeling of medical data.

SUMMARY OF THE INVENTION

Embodiments of the present invention provide methods, systems, computer program products and data structures for hierarchical organization of data associated with medical events in databases. Pursuant to these embodiments, methods of organizing medical data can include hierarchically relating a single type of medical or research event to medical data generated from the single type of medical or research event in a computer database environment. Organizing the data in this way may enable a researcher to access medical data collected as part of a medical procedure performed on a large number of patients, but at different times. For example, the medical data may be viewed in a more hierarchical fashion, thereby enabling the researcher to further investigate potential relationships between other factors.

In further embodiments according to the invention, the received request specifies the single type of medical or research event at the computer database environment and the medical data associated the single type of medical or research event is provided. In some embodiments according to the invention, the medical data can be collected at different times during the single type of medical or research event.

In still further embodiments according to the invention, the medical data can be collected more than one day apart during the single type of medical or research event. In some embodiments according to the invention, the single type of medical or research event can be a standardized group of tests that generate the medical data. In some embodiments according to the invention, the medical data can be pathology data, image data, demographic data, laboratory results data, questionnaire data, cognitive data, physiology data, physician's report data, pharmacy data, medical history data, genotypic data, phenotypic data, microarray data, lifestyle data, diet data, microscopy data, spectroscopy data and/or video data. In some embodiments according to the invention, the medical data can be cross-species medical data. In some embodiments according to the invention, the cross-species data can be human and animal medical data. In some embodiments according to the invention, the medical data can be associated with different ones of the single type of medical or research event for different human or animal subjects.

In some embodiments according to the invention, the medical data can be organized as data structures in a computer database environment embodied in a computer readable medium, that includes a single type of medical or research event object at a first level of hierarchy in a computer database environment and a plurality of medical data objects at a second level of the hierarchy in the computer database environment that is lower than the of the first level of the hierarchy, wherein the plurality of medical data objects are generated from the single type of medical or research event object.

In further embodiments according to the invention, a system for organizing medical data can include a database environment configured to store a single type of medical or research event object at a first level of hierarchy in a computer database environment and a plurality of medical data objects at a second level of the hierarchy in the computer database environment that is lower than the of the first level of the hierarchy, wherein the plurality of medical data objects are generated from the single type of medical or research event object and a processor circuit configured to hierarchically relate the single type of medical or research event object to the medical data object.

Still further embodiments of the present invention provide methods of organizing medical data including obtaining a plurality of instances of medical data associated with a plurality of patients. The instances of medical data includes cross-species medical data. A single type of medical or research event is requested from a hierarchical database environment. The single type of medical or research event is related to the instances of medical data generated during the single type of medical or research event in the hierarchical database environment.

In some embodiments of the present invention, the related medical data associated the single type of medical or research event may be provided to a user. Furthermore, relationships may be established between the provided related medical data and information contained in at least one of a reference source, a research database and a clinical database.

DETAILED DESCRIPTION OF EMBODIMENTS OF THE INVENTION

Figure 1:
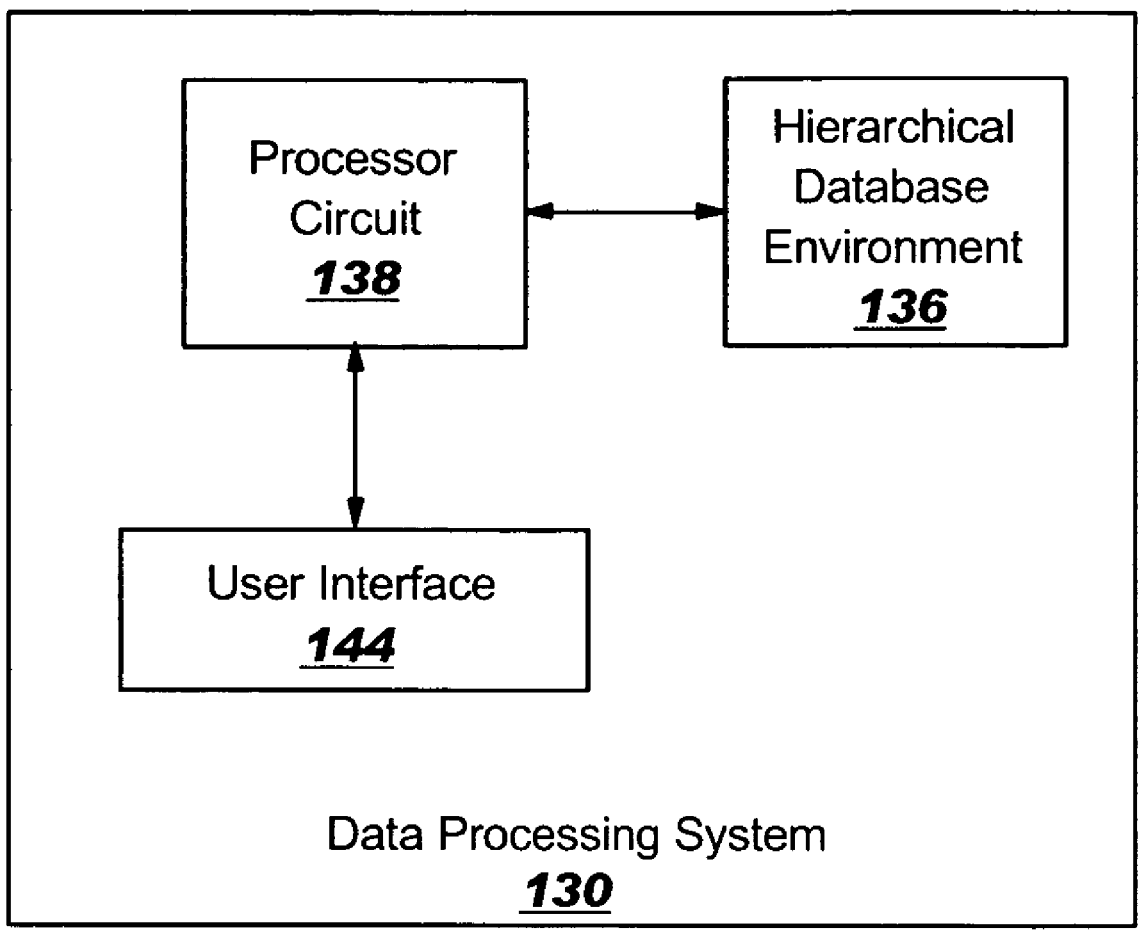
FIG. 1 is a block diagram illustrating systems according to some embodiments of the invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as JAVA®, SMALLTALK or C++. However, the computer program code for carrying out operations of the present invention may also be written in conventional procedural programming languages, such as the "C" programming language or in a visually oriented programming environment, such as VISUALBASIC.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 7. As described herein, some embodiments of the present invention provide a database environment for storing medical data. The medical data may be associated with a single type of medical or research event, for example, a check up thirty days after experiencing a heart attack. In other words, using the database environment according to embodiments of the present invention, stored medical data associated with a single type of medical or research event may be obtained for a plurality of patients. Furthermore, this medical data may be accessed and displayed in an organized fashion so as to allow the data to be analyzed for medical or research purposes as discussed further herein below.

Referring now to FIG. 1, a block diagram illustrating systems, for example, data processing system 130, according to some embodiments of the invention will be discussed. In particular, a hierarchical database environment 136 operates under the control of a processor circuit 138. The processor circuit 138 can be a general purpose processor circuit within a general purpose or application specific computer. As described above, the processor circuit 138 may use elements of both hardware and software to carry out the functions described herein.

The system 130 also includes a user input device 144 may include a keyboard or keypad, a display, microphone, speaker and/or other types of input/output functionality that may enable the user to interact with the hierarchical database environment 136 via the processor circuit 138. It will be understood that the elements shown in FIG. 1 may operate on a single computer system or may be distributed among two or more computer systems that operate in cooperation with one another to carry out the operations described herein. The two or more computers may communicate with one another over a network, such as a local area network.

The hierarchical database environment 136 is configured to store medical data that is generated from medical or research events, such as examinations conducted on patients (living or non-living), research conducted on animals (living or non-living), as well as other types of data that is discussed in greater detail herein. As used herein, "medical data" refers to instances of data collected during a medical or research event. For example, the medical or research event may be a checkup that may include a laboratory test. The fact that the laboratory test took place may be a first instance of medical data or a first medical event associated with the checkup and the result of the laboratory test may be a second instance of medical data or a second event associated with the checkup. By way of further example, the medical or research event may consist of an experiment wherein tissue or cells (human or animal) may be placed on a silicon substrate and medical data may be generated about the tissue or cells using a computer research model. These instances of medical data may be stored separately in a memory of the hierarchical database environment 136. Medical data according to embodiments of the present invention may include pathology data, image data, demographic data, laboratory results data, questionnaire data, cognitive data, physiology data, physician's report data, pharmacy data, medical history data, genotypic data, phenotypic data, microarray data, lifestyle data, diet data, microscopy data, spectroscopy data and/or video data without departing from the scope of the present invention.

In some embodiments according to the invention, the medical data stored in the hierarchical database environment 136 is hierarchically related to a single type of medical or research event that generated the medical data. Accordingly, a user may access the hierarchical database environment 136 to request medical data associated with a single type of medical or research event. Because the single type of medical or research event is hierarchically related to the medical data generated therefrom, the hierarchical database environment 136 can provide the medical data for user access in a more convenient fashion.

In certain embodiments of the present invention, the medical data stored in the hierarchical database environment 136 may be searched and analyzed using conventional data mining tools, such as IMINER, SAS miner and the like. Thus, these data mining tools may be used to identify patterns in the medical data stored in the database, which may possibly be useful in providing a diagnosis. In certain embodiments of the present invention, medical data may be retrieved using query tools, such as SQL, MICROSTRATEGY, BUSINESSOBJECT, COGNOS and the like. Furthermore, some embodiments of the present invention may be used in combination with existing database software, such as DB2 from International Business Machines, Armonk, N.Y., the assignee of the present application. Other database software that may be used in some embodiments of the present invention includes ORACLE from Oracle of Redwood Shores, Calif., SQL Server from Microsoft Corporation of Redmond, Wash. and SYSBASE from Sysbase of Dublin, Calif. The exemplary database software provided herein is provided for exemplary purposes only and embodiments of the present invention are not limited to these examples.

In some embodiments according to the invention, the single type of medical or research events, as well as the medical data generated therefrom, are stored in the hierarchical database environment 136 in data structures that are hierarchically linked. For example, medical data generated by tests performed on different patients can be hierarchically related to one another as both being generated by the same single type of medical or research event that is common to all the medical data that is so identified.

Figure 2:
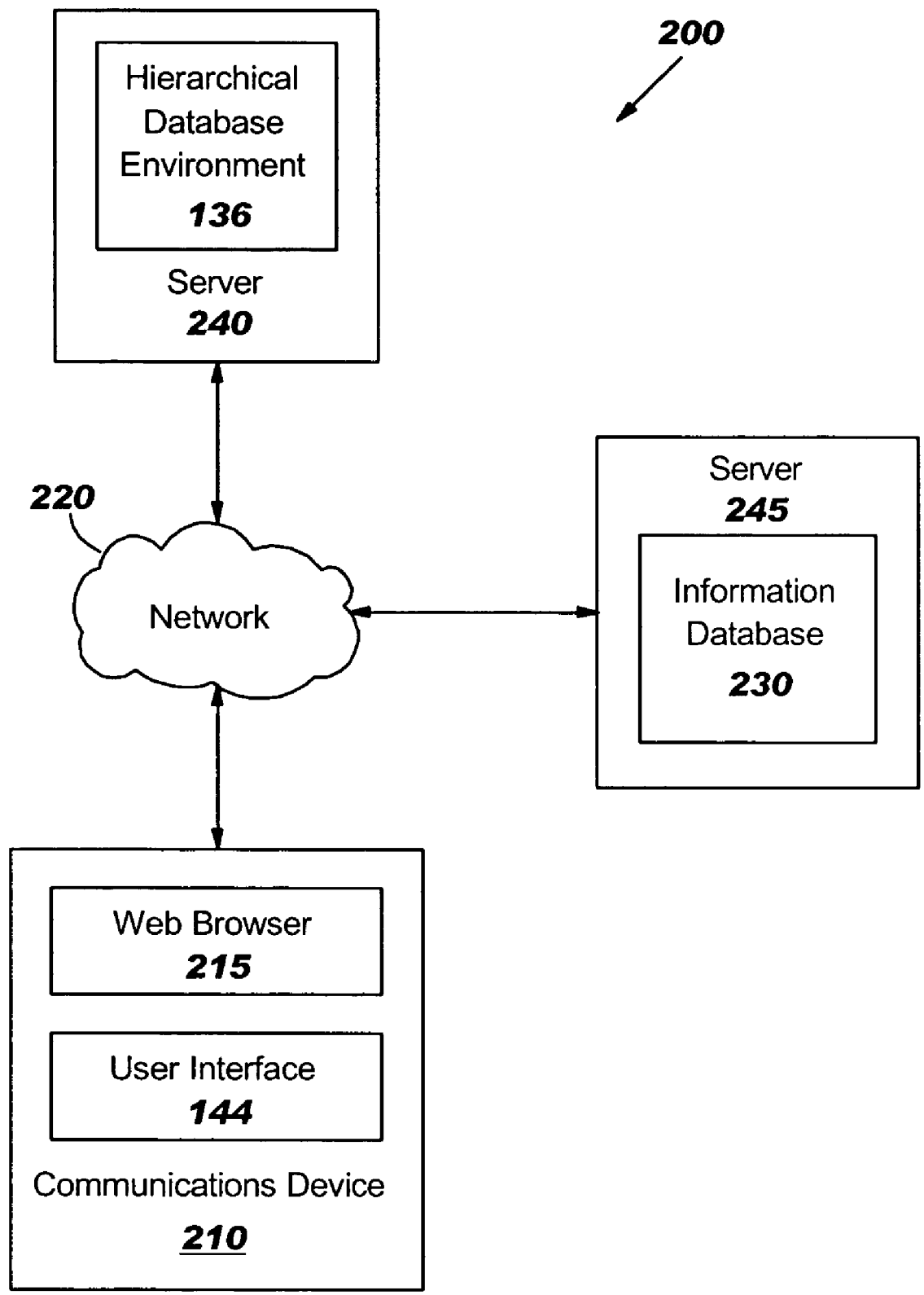
FIG. 2 is a block diagram illustrating some embodiments of the present invention in an exemplary network environment.

Methods of collecting and storing data in databases are known to those having skill in the art and, therefore, will not be discussed in detail herein. An exemplary method of collecting and storing data in databases will be discussed with respect to FIG. 2. A block diagram illustrating an exemplary environment for collecting medical data according to some embodiments of the present invention is illustrated in FIG. 2. As illustrated, the environment 200 may include a communications device 210, a network 220 and first and second servers 240 and 245. The communications device 210 may be, for example, a laptop computer, a desktop computer, a personal data assistant (PDA), a web capable mobile terminal or any device capable of communicating with the network 220. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

As further illustrated, the communications device may include a web browser 215 that may be accessed through the user interface 144. The web browser 215 may allow a physician, nurse, medical technician or the like access to a text or graphical interface used to enter instances of medical data. For example, the web browser may include a graphical interface that requests such information as patient's name, address, phone number, physician's name and location, the date and time and the like. Furthermore, as the instances of medical data, for example, height, weight and blood pressure, are collected during a medical or research event, such as a check up, the instances of medical data may be entered using the graphical user interface on the web browser 215. Once an instance of medical data is entered into the graphical user interface, the physician, nurse or medical technician may indicate that the instance of medical data be stored in the hierarchal database environment 136 by, for example, pressing an enter key on a keypad. The web browser 215 may communicate the instance of medical data over the network 220 to the first server 230, which may then store the instance of medical data in the hierarchal database environment 136 on the first server 240.

Furthermore, a researcher or data miner may also use the web browser 215 to search and analyze the medical data stored in the hierarchal database environment 136. As illustrated in FIG. 2, the second server 245 may include a information databases 230 including, for example, publicly available medical information related to genes, proteins and the like. The researcher or data miner may use this publicly available information to add value to the medical data associated with the medical or research event as discussed further below. The publicly available data may provide statistical support for a proposed diagnosis, context, definitions, a reference source and the like. It will be understood that the environment 200 provided in FIG. 2 is provided for exemplary purposes only and that embodiments of the present invention are not limited to this configuration.

Figure 3:
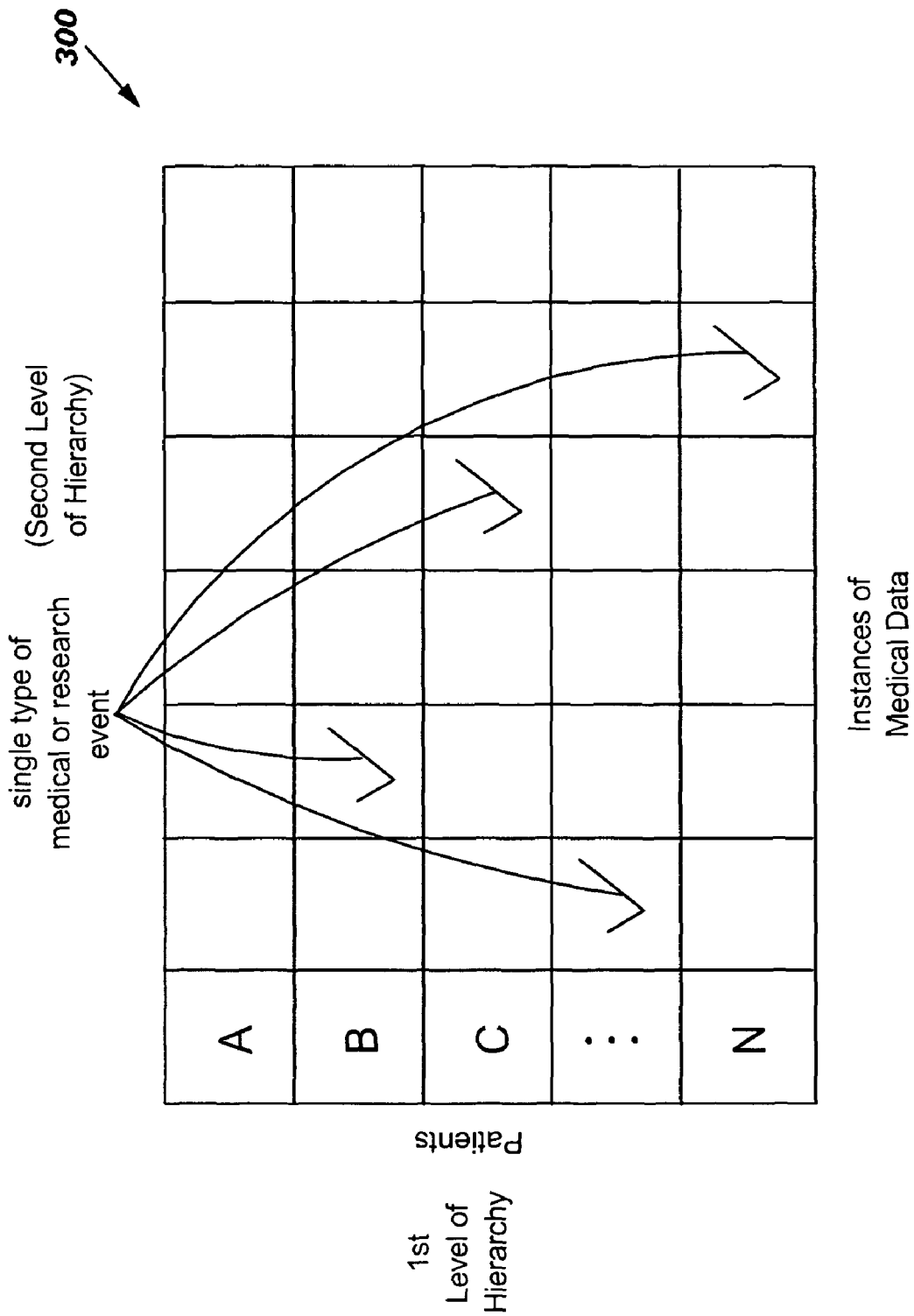
FIG. 3 is a schematic illustration of hierarchical relationships between a single type of medical or research event and medical data in a database environment according to some embodiments of the invention.

Referring now to FIG. 3, a schematic representation of medical data stored in a hierarchical database environment 136 related to a single type of medical or research event data structure according to some embodiments of the invention will be discussed. Table 300 in FIG. 3 shows an unstructured arrangement of medical data for the purpose of illustrating the hierarchical relationship of the data stored therein to a single type of medical or research event data structure according to some embodiments of the invention. As used herein, "unstructured" medical data refers to data that does not necessarily logically fit together well. It will therefore be understood that the unstructured medical data in table 300 is used to describe the hierarchical relationship between the medical data stored therein and the single type of medical or research event data structures.

It will be understood that each of the check marks in Table 300 represents medical data for different patients (A through N) generated as a result of a single type of medical or research event conducted on the particular patient. For example, the check marks may correspond to blood pressure data that was generated during a series of tests conducted as part of a thirty day follow up examination after the patient suffered a heart attack. Accordingly, when the blood pressure data generated as part of the thirty day follow up is placed in the hierarchical database environment, it can be hierarchically related to the single type of medical or research event that generated the data, for example, in this case a thirty day check up after a heart attack.

It will be understood that in some embodiments according to the invention, the medical data generated by the single type of medical or research event can be any type of data that is collected as part of a medical event, such as an examination that generates the associated medical data. Furthermore, the medical data can be generated through a research event, such as an autopsy or animal research. Furthermore, the medical data associated with the single type of medical or research event may be generated at different times despite the fact that the data is hierarchically related to a single type of medical or research event. For example, in the above described example related to a check up after a heart attack, the medical data (i.e., blood pressure in this example) for each of the respective patients may have been generated at different times within the respective thirty day check up. In other words, blood pressure information for one patient may have been recorded thirty-five days after a heart attack whereas blood pressure data for another patient may have been generated twenty seven days after a heart attack. Nonetheless, both pieces of medical data can be related to a single type of medical or research event (a thirty day post heart attack check up) regardless of the fact that they were generated at different times after the respective attacks. The medical data can be part of a standardized group of tests to generate the medical data, such as a check up thirty days after a heart attack.

It will be further understood that the medical data identified using embodiments of the present invention may be further parsed to exclude medical data that may be tainted and, therefore, may not be useful. For example, the medical data collected during a series of tests conducted as part of a thirty day follow up examination after the patient suffered a heart attack may include three blood tests for a single patient, each of these blood tests and the results of these blood tests being instances of medical data associated with the tests conducted as part of the thirty day follow up examination after a heart attack. The results of one or more of these blood tests may be tainted by, for example, drugs that the patient took before the blood test was taken. Once all the medical data, including the blood tests, the results of the blood tests and the drugs the patient ingested on the day of the tests, is in the database, techniques according to some embodiments of the present invention may be used to exclude the tainted tests.

Figure 4B:
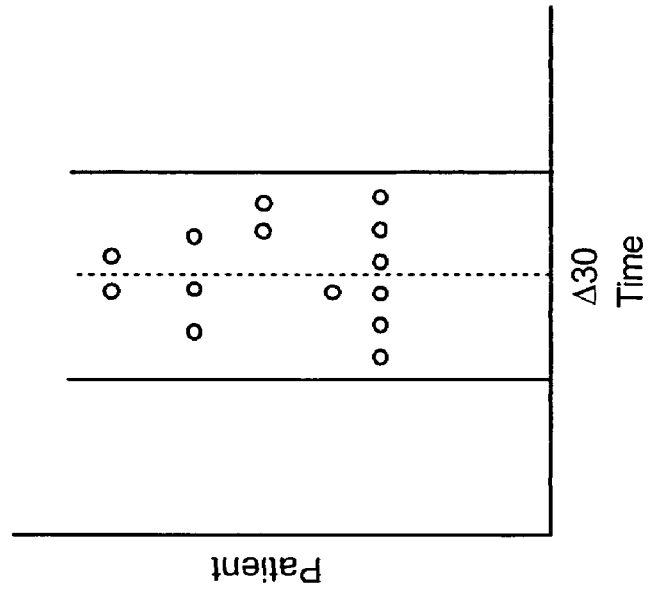
FIG. 4B is a normalized graph of medical data collected from patients suffering heart attacks organized as a single type of medical or research event according to some embodiments of the invention.
Figure 4A:
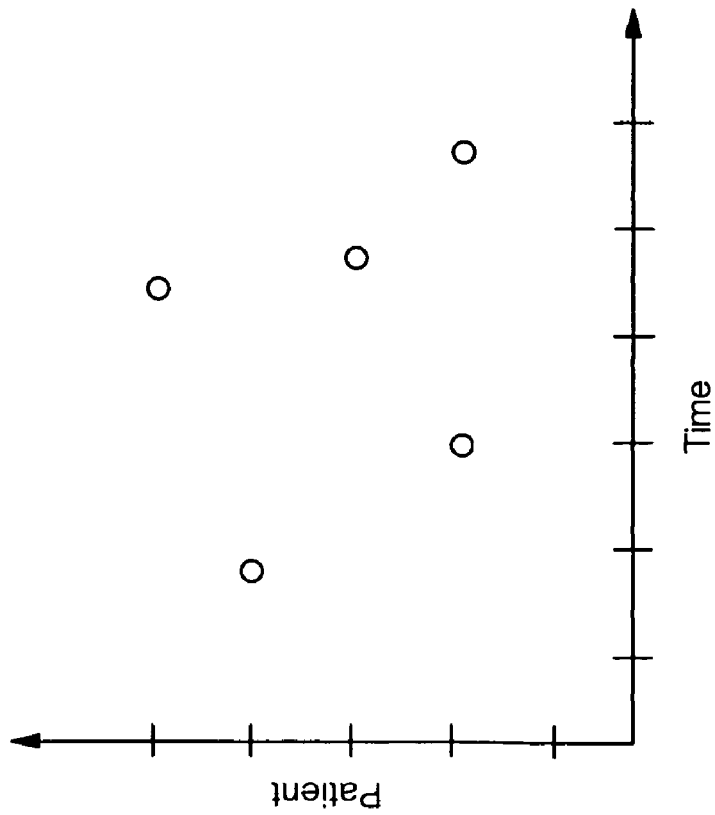
FIG. 4A is a graph illustrating exemplary tests associated with heart attacks in patients over time.

Referring now to FIG. 4A, a graph that further illustrates medical data generated during medical or research events by patients at different times will be discussed. In this example, each of the indicia on the graph represents a different time at which a heart attack occurred in each of the respective patients. A thirty day check up for each of the patients may have been conducted after the occurrence of the heart attack. As shown in FIG. 4A, the medical data generated by tests conducted after the heart attack may occur at very different times and may otherwise be difficult to access in an unstructured database.

FIG. 4B is a simplified graph that illustrates the normalization of medical data generated by a single type of medical or research event (e.g., a heart attack in this example). In particular, the two vertical bars represent a time interval bracketing thirty days after a heart attack. All of the occurrences of the heart attacks indicated by the indicia in the graph in FIG. 4A have been normalized to the y-axis shown in FIG. 4B so that the medical data shown between the vertical brackets around the thirty day check up time frame can all be related to the single type of medical or research event. Furthermore, the indicia shown between the vertical brackets in FIG. 4B around the thirty day check up time frame represent the different times at which individual tests may be conducted on respective patients to generate the medical data. Despite the difference in timing, the medical data shown between the vertical brackets can be considered hierarchically related to the single type of medical or research event (i.e., heart attack in this example).

Figure 5:
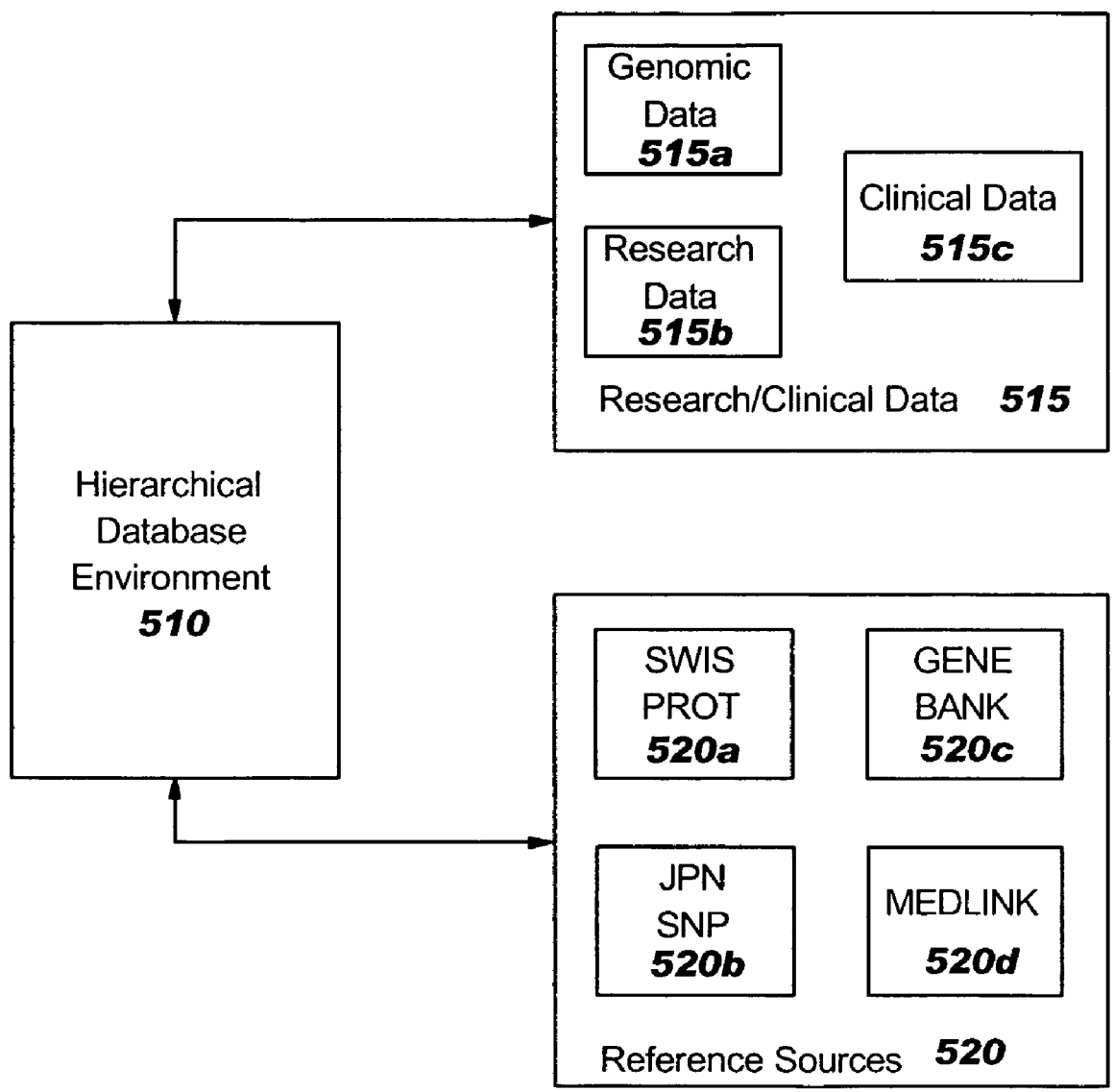
FIG. 5 is a block diagram illustrating operations of systems according to some embodiments of the invention.

Referring now to FIG. 5, a block diagram that illustrates operations of hierarchical database environments according to some embodiments of the invention will be discussed. In particular, a database environment 510 according to some embodiments of the invention can operate as described above and may access a research/clinical database 515, as well as reference sources 520.

In operation, a researcher may operate the hierarchical database environment 510 to identify medical data within the single type of medical or research event to investigate potential relationships among the data for the purposes of, for example, diagnosing a particular condition. In some embodiments according to the invention, the researcher may operate the hierarchical database environment 510 to access HDL data collected as part of a thirty day follow up after a heart attack. By accessing the HDL data in this way, the data may be viewed in a more hierarchical fashion, thereby enabling the researcher to further investigate a potential relationship, for example, between a protein evidenced by the HDL data and a gene by accessing a Swiss Prot database 520a included among the reference sources 520. In other words, the publicly available databases may be used to provide statistical support for new findings obtained using the medical data in the hierarchical database environment 510.

If the data included in the Swiss Prot 520a indicates a potential relationship between a particular gene and the protein, the researcher may further access a genomic database 515a included within the research/clinical database 515 to determine, for example, the potential function of the gene that may be related to the protein included in the medical data that is hierarchically related to the single type of medical or research event identified using the hierarchical database environment 510. In other words, the publically available information in the research/clinical databases 515 and the reference resources 520 may be used to provide statistical support for new findings obtained using the medical data in the hierarchical database environment 510.

It will be understood that the reference sources 520 can include further sources such as a JPN SNP database 520b, a gene bank 520c, as well as a medical link database (MedLink) 520d. It will be further understood that the research/clinical database 515 can further include a research database 515 and a clinical database 515c. The research/clinical databases 515 and the reference sources 520 provided in FIG. 5 are provided for exemplary purposes only and, thus, embodiments of the present invention are not limited to the content of the research/clinical databases 515 and the reference sources 520 provided therein.

Databases according to embodiments of the present invention may allow researchers to access medical data that is generated from, for example, examinations conducted on living patients, autopsies, research conducted on live or dead animals, as well as other types of data that is publicly available, such as research/clinical databases 515 and reference sources 520. For example, within the database, a researcher may have access to coronary disease measurements from anonymous cadaver aortas, specified sets of blood tests from patients having values within a specific range, gene expression via microarrays and images from live patients, test results from lab animals and/or known gene function data from one or more public databases. Thus, according to some embodiments of the present invention researchers may be able to establish relationships among this seemingly unrelated medical data to possibly provide a diagnostic result or at least identify a non-obvious research trail.

Figure 6:
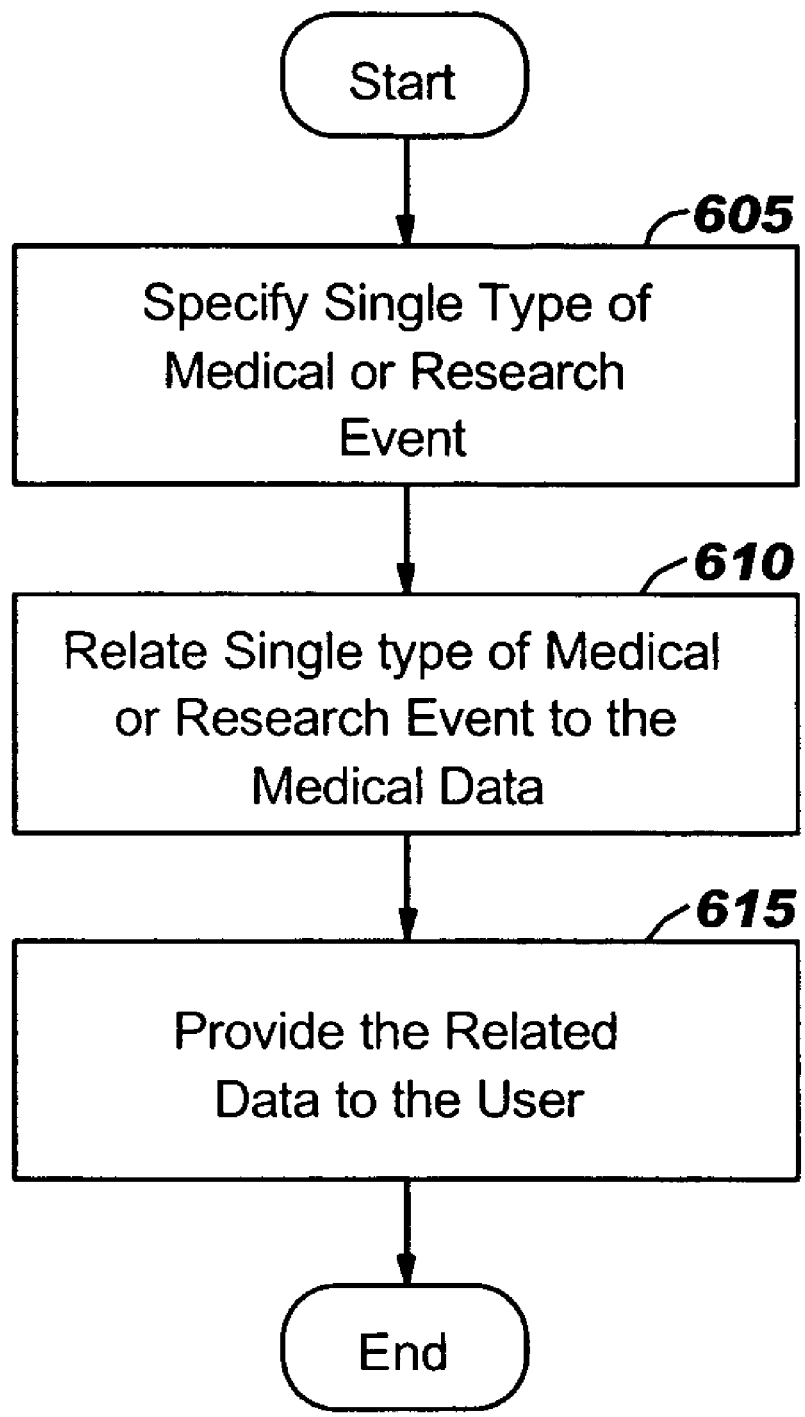
FIG. 6 is flowchart illustrating operations of some embodiments according to the invention.

Referring now to FIG. 6, a flowchart illustrating operations of hierarchical database environments according to some embodiments in the invention will be discussed. In some embodiments according to the invention, a request that specifies a single type of medical or research event is provided to the hierarchical database environment (block 605). As described above, the request may specify any type of medical or research event that is hierarchically related to data generated during or as a result of a single type of medical or research event. For example, in some embodiments according to the invention, the single type of medical or research event can be a thirty day check up after a heart attack in which a standardized group of tests were conducted on patients. It will be understood that some of the medical data may not exist due to the fact that some of the tests may not have been run on the particular patient. In still other embodiments according to the invention, the medical data may be generated as a result of tests conducted at various times during a time interval around approximately thirty days after the heart attack occurred.

The hierarchical database environment can be used to relate the single type of medical or research event to the medical data that was generated by the single type of medical or research event (block 610). For example, in some embodiments according to the invention, medical data generated by tests conducted as part of a thirty day follow up after a heart attack can all be accessed responsive to a request for data related to the single type of medical or research event (e.g., a heart attack in this example). As discussed above, the medical data associated with the single type of medical or research event may be obtained from the database using conventional data mining techniques. Thus, the medical data related to the single type of medical or research event may be provided to the user in a format that can be analyzed to possibly provide a diagnostic result (block 615).

By way of example, a researcher may want to know the variables which best predict, for example, the diagnosis and subtypes of dementia. Thus, the researcher may specify checkups on patients experiencing dementia as the single type of medical or research event (block 605). The hierarchical database environment can be used to relate the single type of medical or research event to the medical data obtained from the patients experiencing dementia (block 610). The information obtained or provided (block 615) to the researcher may allow the researcher to identify, for example, a set of phenotype/genotype parameters that may enable subtyping of dementia, including both rapidly progressing dementia (RPD), as well as slowly progressing dementia (SPD). Accordingly, this information may be used to provide a possible diagnosis.

Figure 7:
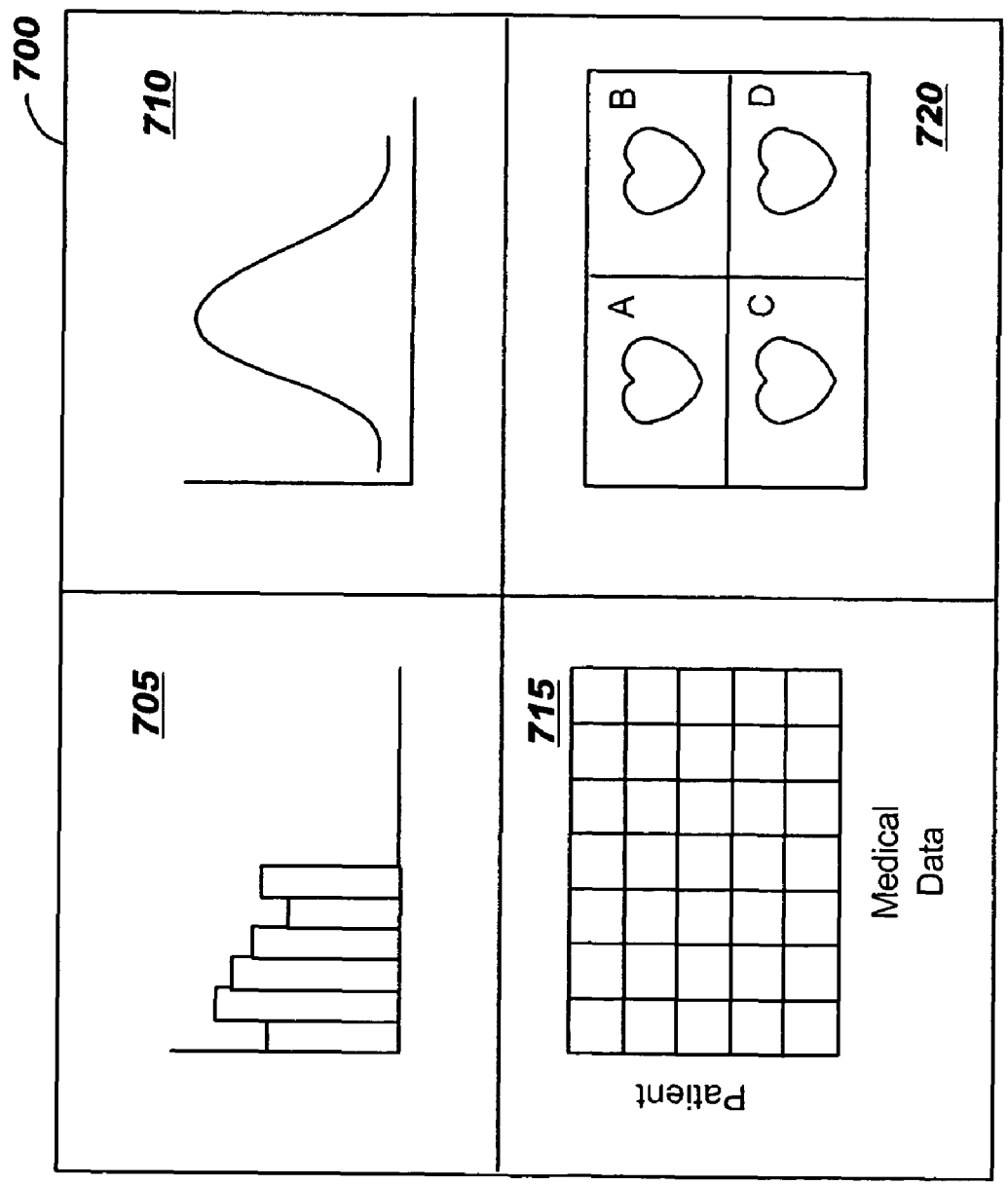
FIG. 7 is an exemplary display of a presentation of medical data associated with a single type of medical or research event according to some embodiments of the invention.

Referring now to FIG. 7, a display that illustrates exemplary presentations of medical data hierarchically related to a single type of medical or research event according to some embodiments of the invention will be discussed. The display may be, for example, the display of the communications device 210 (FIG. 2). In particular, a first portion 705 of the display 700 may represent a histogram that comparatively maps medical data accessed as a result of a single type of medical or research event provided to the hierarchical database environment. The medical data may also be presented in the form of a distribution graph as illustrated in a second portion 710 of the display 700 and/or in a table format as illustrated in a third portion 715 of the display 700. It will be understood that some medical data may not be conveniently displayed in tabular or numerical format, such as images. This type of medical data may be presented as a composite image wherein the image represents a combination of images generated with the medical data that is hierarchically related to the single type of medical or research event specified or a hyperlink may be provided to access this data. Furthermore, a fourth portion 720 of the display 720 may present a plurality of images associated with different patients as part of an array of images included in the fourth portion 720 to facilitate a ready comparison between images, each of which are hierarchically related to the single type of medical or research event. For example, cardiac images of the hearts of patients A, B, C and D are illustrated in the fourth portion 720 of the display 700, which may facilitate comparison of the cardiac images.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A method of organizing medical data in a data processing system, comprising:

hierarchically relating a single type of medical or research event to medical data in a computer database environment embodied in a computer readable storage medium of the data processing system, wherein the medical data is generated from the single type of medical or research event;

receiving, at the data processing system, a request specifying the single type of medical or research event; and providing the medical data associated with the specified single type of medical or research event from the computer database environment of the data processing system to a requestor associated with the request, wherein the medical data is associated with multiple entities.

2. A method according to claim 1 wherein the medical data comprises medical data collected at different times during the single type of medical or research event.

3. A method according to claim 2 wherein the medical data collected at different times comprise medical data collected more than one day apart during the single type of medical or research event.

4. A method according to claim 1 wherein the single type of medical or research event comprises a standardized group of tests that generate the medical data.

5. A method according to claim 1 wherein the medical data comprises pathology data, image data, demographic data, laboratory results data, questionnaire data, cognitive data, physiology data, physician's report data, pharmacy data, medical history data, genotypic data, phenotypic data, microarray data, lifestyle data, diet data, microscopy data, spectroscopy data and/or video data.

6. A method according to claim 1 wherein the medical data comprises cross-species medical data.

7. A method according to claim 6 wherein the cross-species medical data comprises human and animal medical data.

8. A method according to claim 1 wherein the medical data is associated with different ones of the single type of medical or research event for different human or animal subjects.

9. A system for organizing medical data comprising:

a database environment configured to store a single type of medical or research event object at a first level of hierarchy in a computer database environment and a plurality of medical data objects at a second level of the hierarchy in the computer database environment that is lower than the of the first level of the hierarchy, wherein the plurality of medical data objects are generated from the single type of medical or research event object; and a processor circuit configured to hierarchically relate the single type of medical or research event object to the medical data object.

10. A system according to claim 9 wherein the processor circuit is further configured to receive a request specifying the single type of medical or research event object and provide the plurality of medical data objects associated the single type of medical or research event object.

11. A system according to claim 9 wherein the medical data object comprises medical data collected at different times during the single type of medical or research event object.

12. A system according to claim 11 wherein the plurality of medical data objects collected at different times comprise medical data collected more than one day apart during the single type of medical or research event.

13. A system according to claim 9 wherein the single type of medical or research event comprises a standardized group of tests that generate the medical data.

14. A system according to claim 9 wherein the medical data comprises pathology data, image data, demographic data, laboratory results data, questionnaire data, cognitive data, physiology data, physician's report data, pharmacy data, medical history data, genotypic data, phenotypic data, microarray data, lifestyle data, diet data, microscopy data, spectroscopy data and/or video data.

15. A system according to claim 9 wherein the medical data comprises cross-species medical data.

16. A system according to claim 15 wherein the cross-species data comprises human and animal medical data.

17. A system according to claim 9 wherein the medical data is associated with different ones of the single type of medical or research event for different human or animal subjects.

18. A method of organizing medical data in a data processing system, comprising:

receiving, at the data processing system, a plurality of instances of medical data associated with a plurality of patients, the instances of medical data including cross-species medical data;

relating a single type of medical or research event to the instances of medical data in a hierarchical database environment embodied in a computer readable storage medium of the data processing system; and providing related medical data associated with a specified type of medical or research event from the hierarchical database environment of the data processing system to a requestor associated with a request for the specified type of medical or research event, wherein the medical data is associated with multiple subjects.

19. A method according to claim 18, wherein the related medical data is associated with the single type of medical or research event.

20. A method according to claim 19 further comprising establishing relationships between the provided related medical data and information contained in at least one of a reference source, a research database and a clinical database.

* * * * *